United States Patent [19]

Sluijter et al.

[11] Patent Number: 5,433,739
[45] Date of Patent: Jul. 18, 1995

[54] METHOD AND APPARATUS FOR HEATING AN INTERVERTEBRAL DISC FOR RELIEF OF BACK PAIN

[76] Inventors: Menno E. Sluijter, Stadionkade 6, 1077 VG Amsterdam, Netherlands; Eric R. Cosman, 872 Concord Ave., Belmont, Mass. 02178

[21] Appl. No.: 146,875

[22] Filed: Nov. 2, 1993

[51] Int. Cl.$^6$ .............................................. A61F 7/00
[52] U.S. Cl. ........................................ 607/99; 607/113
[58] Field of Search ........................... 607/96, 98–99, 607/100–102, 154, 113; 128/642, 653.1, 654.8

[56] References Cited

U.S. PATENT DOCUMENTS

| | | | |
|---|---|---|---|
| 4,813,429 | 3/1989 | Eshel et al. | 607/102 X |
| 4,907,589 | 3/1990 | Cosman | 607/154 X |
| 5,191,883 | 3/1993 | Lennox et al. | 607/102 |
| 5,281,213 | 1/1994 | Milder et al. | 607/154 X |
| 5,281,218 | 1/1994 | Imran | 607/154 X |

*Primary Examiner*—Angela D. Sykes
*Attorney, Agent, or Firm*—Richard J. Birch

[57] ABSTRACT

The present invention relates to a technique of relieving back pain by heating of an intervertebral disc. The heating is illustrated by a percutaneous technique where a needle or electrode is inserted into the disc under X-ray or other imaging control and subsequently used to elevate the temperature of the disc. Above a certain temperature, the innervation related to the disc is destroyed to the point that back pain related to that innervation can also be eliminated. Specific examples of methods and apparatus to achieve such disc heating are given. Among the methods are use of radiofrequency heating and direct current heating, use of stimulation and impedance monitoring to improve target control, and the use of temperature monitoring to determine and quantify the appropriate disc temperature to achieve the desired clinical results.

14 Claims, 3 Drawing Sheets

METHOD AND APPARATUS FOR HEATING AN INTERVERTEBRAL DISC FOR RELIEF OF BACK PAIN

BACKGROUND TO THE INVENTION

The curing of back pain is one of the most important objectives of neurosurgeons, orthopedists, anesthesiologists and neurologists. Back pain is one of the most common forms of pain and accounts for huge amounts of disability and loss of labor throughout the world. The curing of back pain heretofore has been in the domain of surgery, percutaneous injection of chemicals into the intervertebral disc, percutaneous removal by mechanical means of intervertebral discs, RF heating of peripheral nerves outside of the intervertebral disc to interrupt nerve fibers outside of the disc, and various forms of drug and rehabilitation therapy. Nowhere in the literature of prior art or clinical experience has there been any report or knowledge of placing a probe into the disc for the purpose of heating the entire disc, nor has there been any indication that the heating of a disc to be a safe and effective method of alleviating intractable back pain due to pathology of the disc itself or interrupting of various neural processes in and around the disc. It is the objective and novelty of the present invention that the introduction of a probe or other element into the disc for the purpose of heating the disc provides substantial pain relief in a way which has not been anticipated heretofore.

The use of radiofrequency (RF) electrodes and power sources for generators is common in the field of neurosurgery, anesthesiology, and cardiology for the destruction of neural tissue. This is typified by the RF electrodes and RF lesion generator systems of Radionics, Inc. in Burlington, Mass. Heretofore, the lesion electrodes are placed at the target site under various types of guidance, including stimulation, x-ray control, tomographic image control, and stereotactic apparatus. The electrode typically consists of an insulated shaft with an exposed tip which is elevated to radiofrequency potential. A second electrode, usually a dispersive electrode with a large area, is placed elsewhere on the body to return the radiofrequency current, thereby making the patient's body part of the radiofrequency circuit. The intensity of radiofrequency current at the exposed tip of the radiofrequency lesion electrode causes the heating of the tissue in the neighborhood of the electrode, and thus the destruction of that tissue. Until now, the tissue has always been either direct neurological tissue, such as in the brain or the spinal cord, or muscle tissue, as in the heart in the case of cardiac ablation. A typical example of radiofrequency lesion making is for the relief of various types of back pain, as in the case of facet denervation or in direct destruction of low back nerve structures such as the sympathetic nerves or communicating rami. In the case of facet denervation, the electrode is placed near a small nerve branch which innervates the spinal facet joints, and a heat lesion is made interrupting the noxious signals emanating from these joints. RF heating is also used for destruction of ganglia such as the sphenopalatine ganglion or of other nerves which are ramifiications of the nerves which exit from the spinal column. The mechanism is a direct interruption of nerves and thus of the pain signals from the affected areas to the spinal cord. These procedures have been effective, however, there are many pain syndromes which relate to the region around the intervertebral disc itself. It is very difficult to achieve a comprehensive destruction of the nerves which innervate the disc. This is because the disc is innervated by multiple nerve branches. Some of these branches, notably those which innervate the clinically important posterior part of the disc, lie close to the exiting spinal nerves. Destruction of these branches with a heat lesion would therefore carry the risk of damaging the spinal nerves. It would be a very effective treatment for so-called discogenic back pain to be able to simply and with a minimal number of percutaneous needle sticks denervate or destroy the numerous nerve structures which are present at the surface of the entire disc, without endangering the important nerve structures inside and exiting from the spinal canal.

It has been a characteristic of RF lesion making in the nervous tissue or in the soft muscle tissue that the RF electrode, which affects the heating, be placed in proximity to the tissue to be destroyed. That is, by various stereotactic means, X-ray, fluoroscopy, CT or MR guidance, or stimulation and recording, the tip of the RF electrode is placed directly on or very near the target nerves themselves, and the heating is subsequently carried out. A technique which has heretofore not been done is to place the electrode in a position relatively remote from the nerves to be destroyed, heat an intermediate structure which then carries over to more remote neural structures, and thereby destroy those remote neural structures. That methodology and approach is one of the novel and interesting aspects of the present invention.

Several methods exist which have sought to reduce back pain emanating from the intervertebral disc by removing percutaneously tissue from the disc. The most popular of these methods is the so-called percutaneous discectomy procedure developed by Dr. Gary Onik. In this procedure, a special needle is placed into the intervertebral disc by a puncture through the skin on the back of the patient under fluoroscopic guidance. Once the needle is in place, a mechanism within the needle draws in the intervertebral disc material by a vacuum, cuts it off, and sucks it out by means of a reciprocating cutting element within the needle itself. This effectively reduces the volume within the disc and, if a disc is bulging or otherwise enlarged, the loss of volume will tend to reduce the impingement of the surface of the disc on macroscopic nearby nerves. It will not be effective at destroying the numerous nerves around the periphery of the disc if they are the cause of the discogenic pain.

The present invention relates to a new and novel technique of introducing an RF electrode or other heating electrode into the intervertebral disc, typically under fluoroscopic control, and heating the entire disc to a temperature significantly above body temperature. The heated disc will, in turn, heat the nerves which innervate its surface, and they will be destroyed or altered if the heat of the disc is elevated to an appropriately high temperature.

The prior art of radio frequency lesion generation deals with RF electrodes being placed into tissue such as the brain tissue or muscle tissue, in which the nerve cells to be destroyed actually reside adjacent to the electrode. That is, the tip of the electrode with the active exposed surface, is placed in the vicinity of the nerves, if not in the neural tissue itself. Thus, by applying the radio frequency current, the tissue in the immediate vicinity of the electrode tip is heated and the nerve fibers to be destroyed are thereby killed. This is typically used in the brain for curing of various neurological disorders, such as thalamotomies, and it is also used in other parts of the body, such as in the neck or back region to cure various forms of spinal pain related to disorders of the spinal facets or disorders related to various ramifications of nerves emanating from the spinal column. A background to this technique, which is well known in the prior art, is described in the papers of Cosman and Cosman[1], Cosman, Nashold et al.[2], and M. Sluijter[3,4,6]. The concept of a direct neurological lesion being made by RF heating is well known in medical practice and has been utilized for decades.

As alluded to above, one of the outstanding problems in the treatment of back pain relates to neural structures that innervate the intervertebral disc itself. There are numerous sensory nerves which cluster at the exterior surface of the intervertebral disc and sense mechanical deformations of the disc. These nerves have evolved most probably as a protection mechanism against excessive stress of the disc wall, which in turn may cause serious damage to the disc, such as rupture, bulging, or herniation. In the situation of an overstressed disc, a rupture can cause extrusion or bulging of the inner material of the disc beyond the external wall with consequent pressure on nerves in the vicinity. This is one of the most common forms of back pain, and usually must be cured by surgery or percutaneous disc removal. However, another very common form of back pain related to the disc is the mere irritation or stimulation of the numerous small nerves that innervate the periphery of the disc and sense its mechanical stress. These nerves are found ubiquitously over the surface of the disc. In the situation where herniation or extrusion of the disc has not taken place, yet these numerous tiny nerves are stimulated to produce a painful response, there is no simple surgical treatment, and the patient may be in extreme pain and distress as a result. It may be fruitless to attempt to place an RF electrode directly on these small nerves, as they are distributed over an extensive surface of the disc, making it impractical and dangerous to introduce a sufficient number of electrodes in to denervate all of them. More particularly, it is not possible to know beforehand exactly which of these sensing nerves is causing the problem. Indeed, there may be a large number of them over the entire surface of the disc in the situation that the disc is extremely distorted, or alternatively only a subset of them at one particular location for a more focal disc bulge.

Therefore there exists a need for heating and desensitizing these nerves around the disc by minimal invasion to the body, while at the same time sparing the larger nerve bundles running in the vicinity of the disc. Such a technique would produce significant pain relief in a substantial fraction of patients suffering from back pain. This then is one of the objectives of the present invention.

Another objective of the present invention is a technique for heating and destroying neural structures via an intermediate anatomical body such as bone, cartilage, or in the case of the present invention, the intervertebral disc. Thus the present invention relates to what might be described as an indirect radiofrequency lesion method whereby the destruction of desired neural structures is done not by direct placement of an RF electrode near the structures, but rather by the radiofrequency heating of an intermediate structure, which in turn diffuses the heat to the neural structures in a more diffuse and global fashion. An objective of the present invention is to produce this indirect or global heating of an intervertebral disc so as to relieve diffuse back pain related to innervation of the disc's surface itself. This is a new and unique technique with a new and unique clinical indication for relief of pain which heretofore has been refractory to surgical or percutaneous methods.

Associated with indirect or global radiofrequency heating technique, it is important to be able to monitor temperature, not only at the direct point of RF electrode heating, but also at remote points in space so as to monitor and control the exact temperature distribution. Thus it is another objective of the present invention to provide electrode and temperature monitoring systems to carry out the direct and/or indirect monitoring of points in space relative to the primary RF lesion electrode for safer and more effective control of the heating process.

DETAILED DESCRIPTION OF THE DRAWINGS

Figure 1:
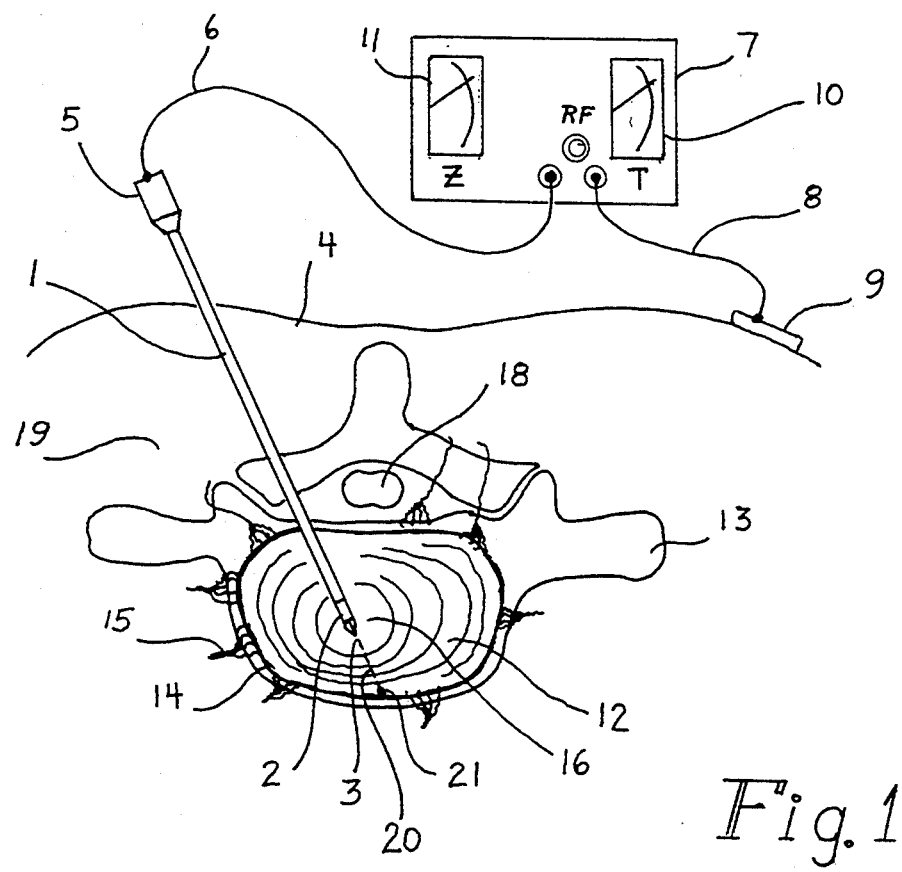
FIG. 1 shows the RF heating of an intervertebral disc according to the present invention, using a single percutaneous electrode.

The papers of Cosman et al.[1,2] and M. Sluijter et al.[3-6] adequately describe the well-known technique of RF electrode heating to destroy neurological structures. This heating has heretofore always been of a direct nature described in the section above. FIG. 1 shows the method and apparatus of the present invention, which involves an indirect heating of neural structures by placement of an RF electrode into the intervertebral disc, so as to relieve back pain associated with innervation of the surface of the disc or nearby structures. This is merely one embodiment of the present invention involving an RF electrode, but could apply equally well to any other probe type which provides heat to the disc.

Referring to FIG. 1, the electrode 1 consists of a rigid shaft which is insulated except for its tip end 2. The tip end has a sharpened point 3, enabling it to penetrate the tissue of the body 4 during percutaneous entry. The exposed metal tip 2 represents the active electrode area. At the hub 5 of the electrode, there is a connection cable 6 connecting to a source 7 of radiofrequency power. This RF lesion generator is typified by the products of Radionics, Inc. in Burlington, Mass. There is also a cable connection 8 to the so-called reference electrode 9 that is typically attached to the surface of the body. This RF lesion connection diagram is referred to as a monopolar type arrangement, meaning that there is a single active electrode tip 2. The reference electrode 9 typically has a very much larger area than the active tip 2, so that there is no heating at the surface of the body where electrode 9 is attached. Radiofrequency generator includes devices and readouts for monitoring the temperature at the electrode tip 2. This is illustrated by the temperature monitoring meter 10. Also monitored is the impedance in the RF circuit through the electrodes as indicated by the meter 11. This monitoring is typical of modern RF lesion generators. The rf generator may also include a stimulator and control circuitry to vary and monitor the radio frequency power delivered to the electrode 1.

One of the novel and unique aspects of the present invention as shown in FIG. 1 is that the RF electrode tip 2 is placed directly into the anatomical intervertebral disc 12. By their nature, the intervertebral discs act as cushions or shock absorbers between the bony vertebral structures 13. Because they are elastic, their surface 14 is subject to stresses, strains, and even injury if the disc is overstressed by excess weight or improper mechanical movements. Such stresses can give rise to the distortion of the disc and of its surface shape. Such mechanical distortions of the disc are monitored by the nerve structures 15 which are located over the surface 14 of the disc. These neural sensing structures are distributed widely over the surface of the disc and are the first warning signs of an overstressed disc surface. An overstressed disc surface can give rise to bulging, herniation or even rupture, which is one of the most common causes of back pain. Thus these neural structures 15 provide natural warning detectors that the disc is being overstressed or injured. Frequently an injured disc will have irritation to its surface and possibly permanent distortion of its surface, which will give, rise to chronic and continuous pain signals from the neural structures 15. Frequently the patient will be normal in all other respects, yet the chronic irritation of the nerves 15 gives rise to chronic and debilitating pain. As mentioned above, it is impractical to consider knocking out each of these neural structures by multiple placement of numerous RF electrodes near each of them, as in the case of a direct RF lesion techniques done in the past.

The novel and unique discovery of the present invention is that by placing even a single RF electrode in the interior region at the position 16 approximately at the center of the disc, and then heating the region of the interior disc by applying RF power there, one essentially achieves a global spread of heat throughout the disc. This heat then causes heating of the neural structures 15 which innervate the surface of the disc. If properly done, preferably with the monitoring of temperature, this process can denervate the neural structures 15 on a global or semi-global basis, relieving the patient of back pain related to stress of the intervertebral disc and its surface.

Placing an RF electrode in the interior of a disc as shown in FIG. 1 has not been demonstrated or reported for this purpose in the prior art, and it is also not obvious a priori that it will have any substantial effect on pain relief. Previous investigators have attempted to decrease back pain by percutaneously introducing needles into the intervertebral disc and either injecting chemicals or using mechanical means to remove intervertebral disc bulk material. By so removing such material, one can relieve mechanical stresses on the disc, and thus relieve stress on the surface of the disc, which in turn can in some cases relieve back pain. Thus, the technique of placing probes into the intervertebral disc is well known. What is not obvious, as revealed in the present invention, is that by applying heat to the intervertebral disc one can globally and indirectly denervate nerves which cause serious back pain. Heretofore, it has always been practiced that direct placement of the electrode in the vicinity of the nerves is the way to make an RF neurological lesion. Indeed, it is one of the novel discoveries and inventions of the present patent that the method of heating the interior of the disc will cause effective heating throughout the disc in such a fashion as to destroy the neural structures 15, yet not give rise to substantial pain to the patient during the lesion heating process. One explanation for this important discovery is that the evolution of neural structures 15 innervating the surface of the disc has been devoid of temperature sensing nerves since the disc is at core body temperature. Thus the need for temperature sensing neurological structures on the surface of the disc has probably been abandoned by the process of natural selection. It appears that only pressure and pain sensing fibers 15 have remained on the surface of the disc, and that these can be destroyed by the heat method of the present invention without substantial discomfort to the patient during the heating process. This latter point is only speculation, however, in practice it has been demonstrated that intervertebral disc heating with dramatic relief of back pain related to neural structures innervating the disc is very effective and safely done and is devoid of any direct pain to the patient during the procedure itself.

Another novel feature about the method of the present invention relates to the nature of the target region and how it responds during rf heating. The space in the intervertebral disc is of a very special structure and consists of a fibrous material with a substantially low electrical impedance. It is believed that the fibrous intervertebral disc material is not innervated directly, and there is no blood supply there. Thus the present invention introduces the concept of the "indirect" RF lesion. Specifically, the RF active tip 2 is placed in anatomical tissue which has no neural structures in the immediate vicinity of the tip, nor any direct proximal blood supply. Thus, it is the heating of the entire medium of the disc itself which causes the indirect or global heating of the neural structures 15. It may also be the case that there are other neural structures which run close to the surface of the intervertebral disc which will also be heated indirectly by the intervertebral disc core heating. The obliteration of these nerves as well may also be another factor in the pain relief achieved by the present invention.

The physical basis for the present invention is that heat produced at the core of the intervertebral disc is spread out over a substantial distance throughout the disc so as to heat its periphery. The reason that the heat can spread so effectively to such a long range is that the intervertebral disc material has no vascularity. Because there is no blood flowing in the disc, the usual dramatic convection of heat away from the heated region is reduced essentially to zero. In this respect, the disc is strikingly different from all other rf lesion targets that have been heretofore heated. Other targets, such as the brain, spinal cord, muscle tissue, etc., are all highly vascular. Thus the usual diminution of heating at long range associated with heating the brain tissue and muscle tissue is absent.

A second factor which enhances the global heating of the entire disc is that the disc represents essentially a two-dimensional layer between the bony vertebrae above and below it. The bone is a good thermal insulator and also is not as highly electrically conductive as the disc or normal tissue. Thus the electrical current from the active tip 2 will tend preferentially to spread only throughout the disc, and much less through the bones above and below it. Heating thereby done within the disc is confined to the disc as a consequence of the insulative character of the bones above and below it. Thus, the heat spreads quickly and effectively through the entire disc, raising the entire pancake-shaped structure of the disc to high temperature. The heat flows to the periphery of the disc where it heats the neural structures and other surrounding tissue. It is only at the disc periphery that vascularity or convective flow enters the equation of heat balance, and essentially only there the heat is sinked away rapidly in the annulus of tissue immediately outside the surface of the disc. Thus one can expect an elevated temperature throughout the disc with a rapid fall-off of temperature as one emerges from the surface of the disc into the surrounding tissue. However, it is just in that critical range of the surface of the disc where the temperature can remain elevated, thereby destroying the innervating structures of the disc, and yet not endangering other critical structures, such as the spinal cord. 18, that may be in the vicinity of the disc. Any substantial heating of the spinal cord 18 could cause severe danger and injury to the patient, including life threatening neural interruption. However, by the indirect process of heating the non-vascular disc with rapid fall-off of temperature by blood circulation immediately outside the disc, such critical neural structures as the spinal cord 18 and other neural structures, such as the anterior and posterior nerve roots, will not be injured by this process. The fact that the procedure is safe and effective is not at all obvious a priori in view of the fact that such a large structure is being heated to significantly elevated temperatures. It is testimony to the surprising and novel aspect of the present invention and method that the technique in fact does work well.

A typical procedure would be to place the electrode I percutaneously through the surface of the patient's skin 4 under X-ray or fluoroscopic interactive guidance. By taking lateral and anteroposterior views, it is easily ascertained that the proper path of introduction of needle 1 is achieved and that tip 2 resides near the central position 16 of the intervertebral disc. RF current is then applied from the rf generator 7 via the cable 6. The current enters the disc, spreads out through the disc material, and returns out through the body to reference electrode 9 and then through the cable 8 back to the RF generator 7. Thus the patient's body is part of the RF circuit. The temperature at the electrode tip 2 is monitored by temperature meter 10. This can be implemented by a thermal sensor built into electrode tip 2 together with appropriate sensor wires in 6 and circuitry in apparatus 7. A typical procedure might involve raising the core temperature of the disc to 70° C. or more. There will be some fall-off of temperature in the disc out towards the perimeter of the disc, but nonetheless the surface of the disc will be elevated to substantial temperatures 50° C. or 60° C. and perhaps higher. These are sufficiently high temperatures to denervate the fine nerve endings 15 which cover the surface of the disc, thus relieving the patient of pain, but not inducing any pain during the procedure itself.

One interesting and important aspect of the present invention is the discovery that the electrical resistance, or impedance, of the intervertebral disc material itself is substantially lower than surrounding tissue, illustrated in FIG. 1 as the medium 19 that surrounds the entire spinal column. Thus, in the progression of introducing the cannula 1 through the body surface 4, one will observe an impedance which is initially relatively high. Then as one enters the disc space, one sees an immediate reduction of the impedance due to the lower electrical resistance of the intervertebral disc itself. This transition between the normal tissue and intervertebral tissue is direct evidence that the tip of the electrode is in the disc, and thus in a proper position. Furthermore, when the probe is advanced along a path indicated by the dotted line 20 to the point 21 where the tip has reached the far wall of the disc, one can again observe an increase of impedance. This increase would indicate that the tip of the electrode is emerging from the other side of the disc. Thus, one has by impedance monitoring a direct measure of introduction of probe 1 into the disc and the total traversal and limits of the probe tip 2 in the disc space. This represents an important secondary aspect of the present invention related to introduction of the needle into the target volume itself and monitoring means to confirm the process.

Another target method which is of usefulness in the present invention is using stimulation voltage on the electrode as the electrode is advanced through the tissue and on into the disc. Most lesion generators 7 have a built-in stimulator to stimulate neurological structures. By applying the stimulating as one advances the probe, first through the intervening tissue 19 and then on into the intervertebral disc volume, any approximation to critical nerves on that pathway may be detected by continuous stimulation and consequent physiological or motor response. Once the electrode is within the disc volume, because there is no innervation of the interior of the disc itself, all stimulated responses would be absent.

Figure 2:
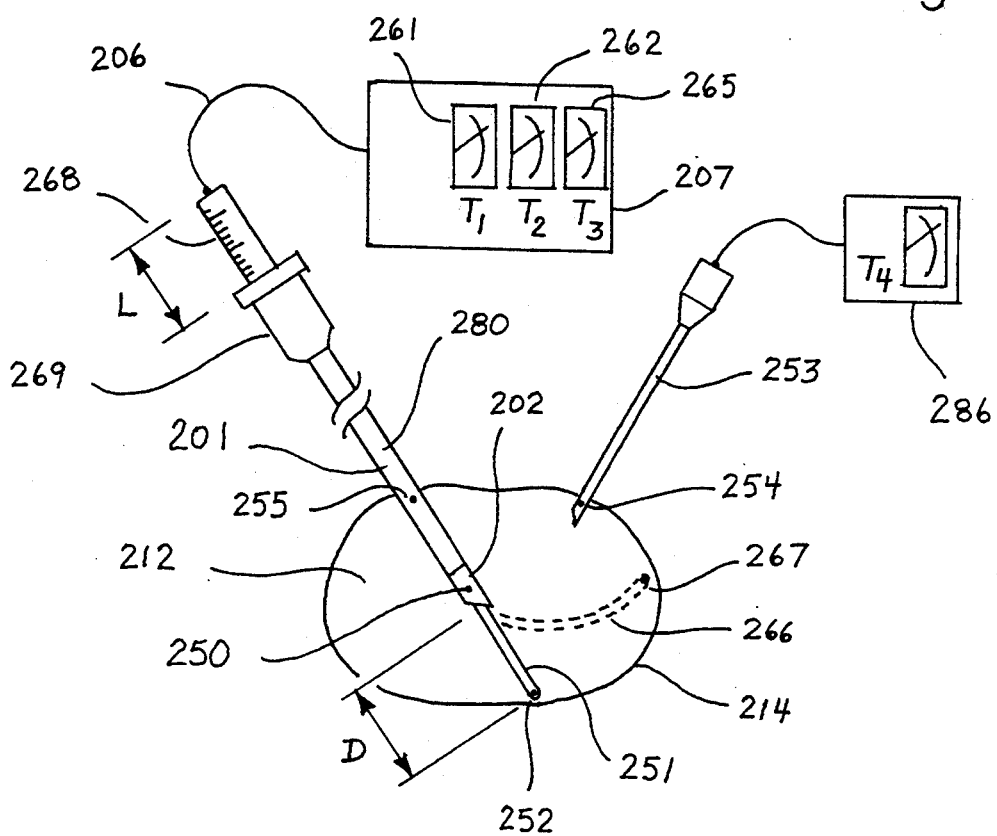
FIG. 2 shows an embodiment of the present invention involving a heating electrode in the intervertebral disc and secondary temperature sensing probes to monitor positions remote from the primary RF electrode lesion site.

FIG. 2 illustrates embodiments of temperature monitoring at multiple positions associated with the present invention. The probe 201 again is inserted into the intervertebral disc space 212. The exposed tip 202 of the electrode is positioned at or near the center of the disc. The shaft 280 of the electrode, except for the tip 202, is usually insulated to prevent heating of tissue other than that near the probe tip 202. Again, the cable 206 enables application of RF voltage to the electrode, and thus heating of the core of the disc.

Because the invention relates to global heating of the disc to destroy neural structures at long range, it may be important to monitor temperature both at the core heating position, namely the point 250 of the electrode tip 202 as well as other points on the surface 214 of the disc.

To illustrate how remote thermometry might be done, an extension tip 251 emerges from tip 201 of the electrode and has a temperature sensor in its tip 252. The tip 252 is shown in proximity to the external surface of the disc, and thus measures the temperature at that point. By this means, the temperature can be monitored at the core position 250 where the primary heating is being done, but also can be monitored at remote point 252 at the surface of the disc which is critical to the denervation of the disc nerves.

Another method of monitoring temperature of the disc is by having a separate temperature monitoring probe 253 inserted along another route. It may measure the temperature at the position 254 at another point on the surface of the disc. This probe could be totally insulated so as to reduce perturbations of the radiofrequency current. Alternatively, it could be a second RF electrode used in a bipolar arrangement with the primary electrode 201 or as a secondary primary active electrode in the field of the disc.

It is also possible to move the extension temperature probe 251 backwards and forwards over a range. If the probe 251 is extended to a distance D beyond the tip 202, then the entire distance of that range can be monitored. For example, if temperature meter 261 measures temperature T1 at tip 202, then temperature meter 262 could measure the temperature T2 at position 252. Similarly, the probe 252 may be withdrawn back up inside of the shaft 201 to a position such as 255. This position is at another point on the perimeter of the disc. The sensor 252, when drawn back to that position, could monitor temperature T3 at a second point on the perimeter and be visualized on yet another temperature meter 265. The independent probe 253 may be monitored by temperature meter 266 on a separate apparatus or an apparatus combined in the RF lesion generator 207.

Yet another way of measuring the temperature throughout the disc and at remote positions would be to have a side outlet probe 266 with a temperature sensor in its tip 267. Such a side probe could emanate along a curved trajectory (as indicated by the dashed line) to access and sample temperatures at points transverse to the probe axis. The degree of extension of any of these temperature probes could be gauged by the scale 268 on the hub 269 of the electrode 201.

It may also be possible to implement the electrode 201 to have a curved or flexible tip structure that can access the entire volume of the disc and thus deposit the primary heat at different locations within the disc. This has been illustrated by the TEW electrode of Radionics and could be applied in the context of the present invention. Another illustration of such a curved or side extending electrode for RF heating is shown below.

There are various embodiments of the needle apparatus which are advantageous to the disc heating procedure. Some embodiments of such needle apparatus which are part of the present invention are shown in FIGS. 3, 4, 5, and 6.

Figure 3:
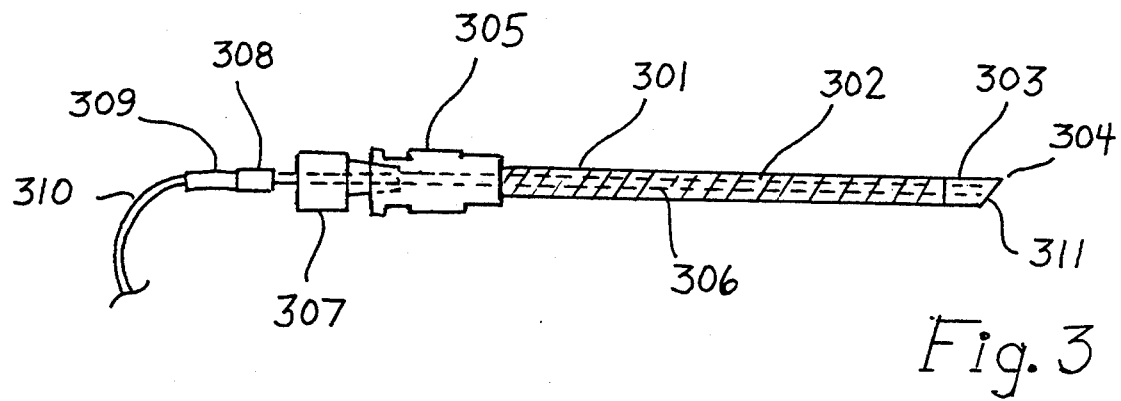
FIG. 3 is a schematic diagram showing an embodiment of electrode apparatus for intervertebral disc heating, including special hubs and cable connections.

Referrring to FIG. 3, there is a cannula 301 which has an insulated shaft portion 302 (illustrated by the hatched surface) with exposed uninsulated tip 303 that has a sharpened, beveled point 304 for penetration of the body into the disc. The hub of the cannula 305 is made from plastic or low radiopacity material so that imaging along the direction of the needle, the so-called "tunnel vision," or "needle view," can be implemented with minimal obstructive artifact from the hub. This is described in the papers of Sluijter et al.[5] Further, there is a stylet system which closes off or obdurates the open lumen of the cannula during the insertion and possibly lesioning phase. This stylet shaft is indicated by the dashed line 306, and said shaft extends down to the exposed tip 303 and may or may not have an angled bevel itself so as to appropriately close off the open lumen of tip 303 during the insertion phase. The stylet has a hub 307 in this illustrative embodiment, which attaches mechanically to the stylet 306. Further, the stylet, which is preferentially made of a conductive metal material, has a connection means 308 which can be coupled by cable connector 309 to a cable 310 which can be further connected to external apparatus, as described above and in FIG. 1 and 2. The hub 307 again may be made from a plastic material in a preferential embodiment of the invention so that the tunnel vision view under X-ray or fluoroscopy can be done with the stylet 306 fully in place in the cannula. One has the advantage of a low radiopacity for the majority of the hubs 307 and 3015. During the procedure the cable 310 may be connected to the external power source, and can supply the radiofrequency or direct current heating power, which emanates through the uninsulated tip 303 into the surrounding bodily tissue (in this case, the intervertebral disc material) to cause frictional heating in that nearby or proximal tissue surrounding the tip. In addition, the electrical cable 310 may be used to sense impedance at the electrical tip 303 during the insertion process. That is, because the inner stylet 303 is conductive, it will make electrical contact with the conductive shaft needle 301, and thereby the tissue impedance of the tissue proximal to the exposed tip 303 may be monitored by appropriate apparatus in the external radiofrequency generating system. It is also possible that at the tip 311 of the obdurating stylet, there can be installed a temperature sensor. Thus, in such a configuration, after appropriate impedance monitoring, X-ray target confirmation, etc., the radiofrequency power can be applied through the cable 310, and the temperature of the tissue surrounding the tip 303 may be monitored during the heating process by the temperature sensor 311.

The electrode system illustrated in the embodiment of FIG. 3 is novel and substantially different from any radiofrequency or other heating electrode systems that have been produced in the past. The electrodes for percutaneous cordotomy, trigeminal neuralgia, and brain lesioning, which are illustrated in the product line of Radionics, Inc., have embodied the use of impedance monitoring, insulated carmulae, indwelling temperature sensors, and cable connection means. However, the configuration in FIG. 3 has a unique combination of several new aspects which make it usable, safe, and effective for the disc heating procedure. Specifically, it is the combination of substantially radiolucent hubs on the cannula and on the stylet used in combination that make the tunnel vision possible while eliminating the need for interchange of stylets, lesion electrodes, impedance electrodes, and cable connections. Thus, the system in FIG. 3 is a compact and maximally efficient electrode system for the intervertebral disc procedure. No combination of the features described for FIG. 3 have been incorporated into a radiofrequency or other heating electrode system in the prior art.

Figure 4:
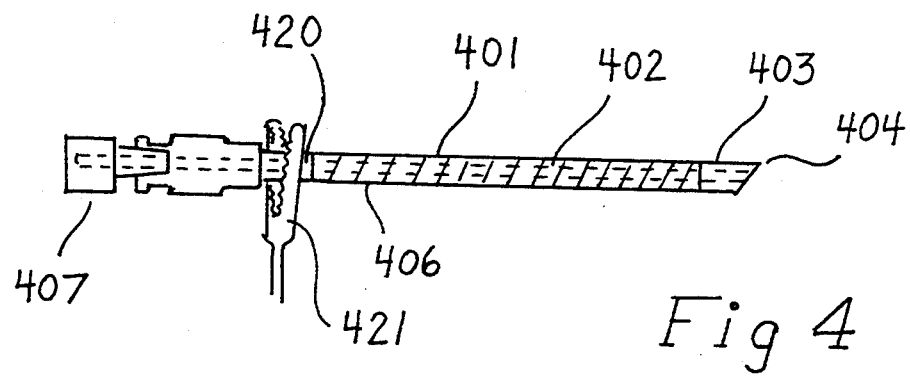
FIG. 4 is another embodiment of needle apparatus for intervertebral disc heating, including proximal connection means for impedance monitoring during needle insertion.

Referring to FIG. 4, there is shown another embodiment of the present invention which shows a variation of the proximal impedance connection means on the shaft of the electrode which makes it possible to insert the electrode into tile body while continuously monitoring impedance, and at the same time having an indwelling, obdurating stylet. The electrode 401 has an insulated shaft 402 and uninsulated tip 403 with beveled point 404. In this situation, a stylet with shaft 406 closes off the lumen of the needle 401 down to the end of the distal tip 403. It again has a radiolucent hub portion 407. In this situation, there is in addition an uninsulated portion of the shaft 420 at the uppermost region of the shaft which will not be implanted in the patient's body. This uninsulated portion can be electrically connected by various connection means, one illustration of which is an alligator type connector 421. The surgeon can insert the needle, therefore, into the patient's body with the electrical connection 410 leading to an impedance monitor, and thereby monitor the impedance continuously as the electrode traverses the external tissues and goes on into the intervertebral disc.

Figure 5:
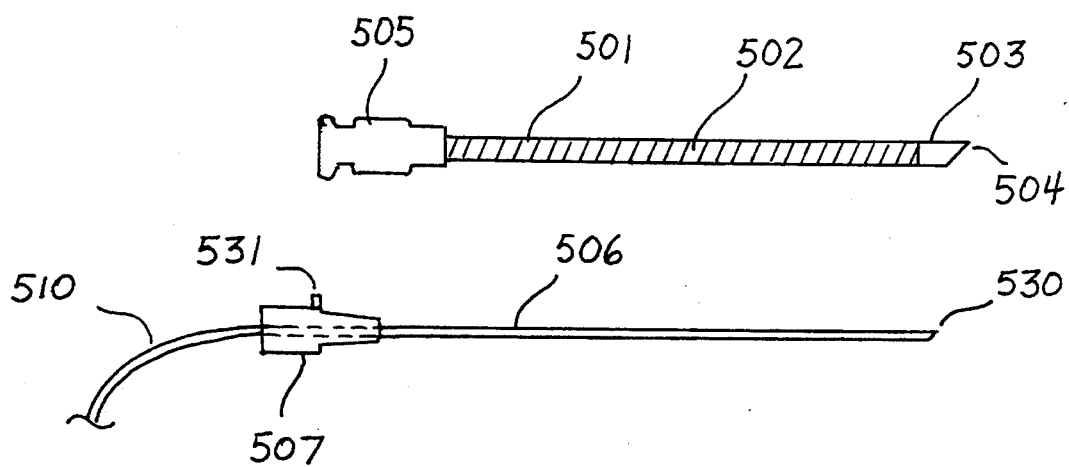
FIG. 5 shows a set of apparatus for intervertebral disc heating, including a radiofrequency cannula with insulated shaft, exposed tip, and plastic hub, together with a universal stylet which has external connection means and impedance monitoring means, and thermal sensing within its tip.

FIG. 5 shows yet another embodiment of the present invention apparatus. A needle 501 with insulated shaft portion 502 and exposed electrical tip 503 has a hub 505 which is made from a radiolucent material such as plastic. The tip is shown with a beveled point 504 for purposes of illustration. It should be noted that this cannula, with open lumen, need not have a sharpened point, but rather may be a square, open lumen. In such a situation, the obdurating stylet may have a sharpened point, which will enable effective penetration of the system of cannula plus styler into the body. Shown as a separate part of this needle system is the inner styler 506, which has in a preferential embodiment a conductive metal shaft. Shown in this figure is a beveled tip 530, which has the same bevel angle as the beveled point 504 of the respective cannula. In such a situation, the radiolucent hub 507 would have a key 531, which would mate to a corresponding notch (not shown in this figure), such that when the stylet 506 is inserted into the needle 501, the beveled ends of the stylet and the needle will be at the corresponding angle, such that the tip of the combination set is flush as it presents to the patient's tissue. Again, the stylet is illustrated with a connection cable 510, which may be connected to external apparatus such as impedance monitoring, stimulation, radiofrequency or high-power heating, and a temperature monitoring apparatus.

The present invention claims the use of such unique combination of needle and stylet. The combinations of needle and stylet per se is not a new concept. For example, the SMK Sluijter-Mehta needle set, produced by Radionics, Inc., has a cannula with insulated shaft, radiolucent plastic hub, and a stylet with a metallic obdurating stylet with radiolucent hub. However, in the SMK set, and in all other electrodes of the prior art, there is no integral means for electrical connection to the obdurating stylet for introduction into the patient's body. Again referring to the SMK Kit, there is explicitly in that kit a separate cannula with radiolucent hub; a separate styler with non-electrical connection, but with a radiolucent hub; and a separate third element: the SMK-TC Thermocouple Probe. The thermocouple probe has electrical connections for providing the radiofrequency current connection to the cannula and for temperature sensing at the tip. However, it is explicitly inserted only after the electrode with obdurating stylet has been inserted into the tissue, and the obdurating stylet removed. The reason for this is multi-fold. First, the obdurating stylet has a sharpened, beveled tip which matches the beveled point of the needles. The SMK-TC Probe, on the other hand, has no such beveled tip, nor is designed to properly occlude the front-facing lumen of the needle. Specifically in the Radionics instructions for use of the SMK Kit, it is disallowed that the SMK-TC Probe be inserted, except after the needles is fully in place. Various adverse consequences would result in insertion of such a probe which is improperly designed for the obdurating function. Coring of patient tissue into the cannula point would result, and damage to the SMK-TC Probe itself could be a consequence. Furthermore, the SMK-TC Probe, as shown in the SMK Kit, has a metal hub which is not radiolucent, and thus not suitable for the "tunnel vision" phase of the needle insertion. Thus, the present invention, with its particular combination of components, circumvents the deficiencies of the SMK Kit and other electrode systems of prior art for the most efficient use in this disc heating application.

Figure 6:
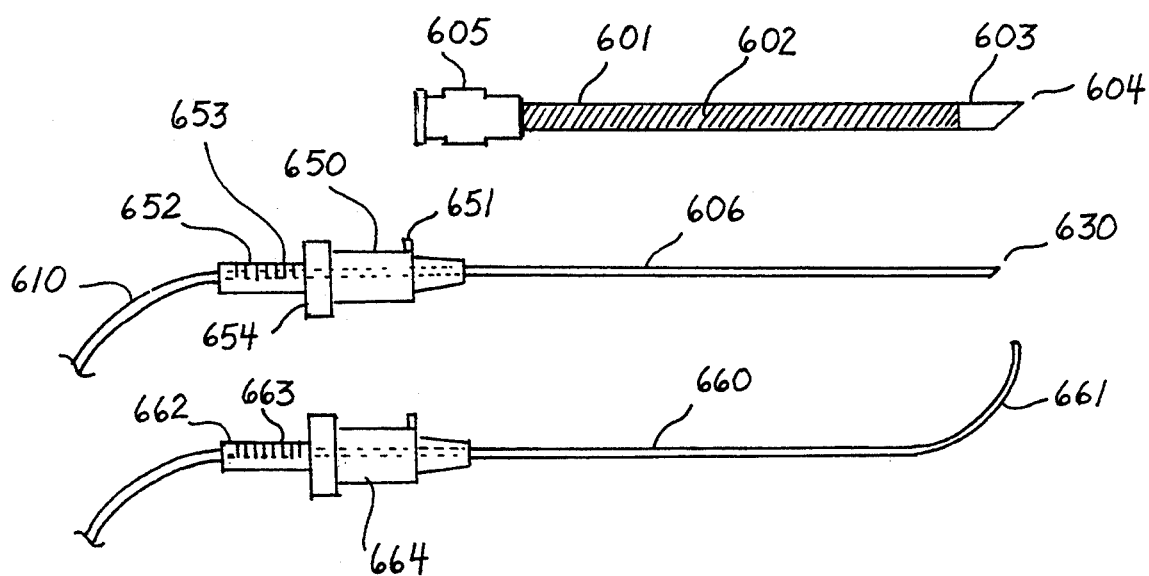
FIG. 6 shows a set of cannula plus straight and curved electrodes to make axial or off-axis heating patterns in disc lesioning.

FIG. 6 shows yet another apparatus embodiment of the present invention. Again, it is a set of instruments which have appropriate design for the disc heating application. Cannula 601 has insulated shaft 602, with exposed tip 603 and sharpened point 604. It again has radiolucent hub 605. Also shown is a straight, multipurpose stylet 606 with appropriate beveled point 630. When this stylet is inserted, appropriately the bevels 630 and 604 will line up so that they are flush and present a smooth surface to the tissue that is being penetrated. In this embodiment of FIG. 6, the hub has another novel feature. There is an outer hub 650 which is of radiolucent material and has the key 651 that is timed or aligned with an associated slot in the needle hub 605 (said slot is not shown in this diagram) so that the bevels 604 and 630 will line up appropriately. Further, it has a secondary adjustable hub 652 which is made of radiolucent material and has measuring markers 653 on it. The user, by observing these measuring markers relative to, for example, the proximal face 654 of the primary hub 651, may be able to determine, while the electrode is in place in the body, the degree of extension of the stylet hub 630 relative to the needle hub 604. This would be appropriate for the geometry shown previously in FIG. 2 where the inner structure may be extended beyond the distal end, or farthest end, of the needle so as to make extended lesions or extended impedance or thermal measurements within the disc itself. Thus, the straight stylet structure shown in FIG. 6 is analogous to the straight stylet structure shown in FIG. 5, with the exception that it has the depth gauge adaption. In addition, a cable means 610 is also illustrated for connection to the external apparatus. It is notable that the beveled front aspect of this straight stylet, together with its radiolucent hub, clearly distinguishes this structure from the structures of the SMK Kit, which have no such adaption means that would make the SMK Kit suitable for this disc application.

Further in FIG. 6 is shown a curved stylet with shaft portion 660 and distal or end portion 661, which has a curve. This curve may be either permanently set into the stylet or may be steerable by adaption means on the hub. Primary hub 662 is analogous or identical to the hub 650 of the straight stylet. Again, depth gauge means 662, with depth markers 663, are provided for the operator to gauge the degree of extension of the curved tip. This would be exemplified by the illustration of FIG. 2 for extended off-axis measurements or heating. Such off-axis heating would be appropriate when difficult approaches to the disc are required. An example of this would be the L5-S1 disc, which, in some cases, requires the needle to be placed in a direction that is not passing through the center of the disc. In such a situation, the needle tip may be off-center from the disc, yet the side extension curve, such as 661 of the inner stylet, may be directed off-axis to bring the average center of lesioning back to approximately the center of the disc. This combination of instruments in FIG. 6 represents yet another specific apparatus embodiment which would be suitable for the disc heating procedure.

This invention is not limited to back pain, but may be applied at any of the intervertebral disc levels from the top to the bottom of the spine. For example, it can be used in treating thoracic or neck pain at the appropriate spinal levels. The invention is also not restricted to percutaneous needle placement. For example, in the process of doing an open surgical laminectomy, which is a very common procedure, a surgeon may wish to insert such a probe or electrode as has been described herein directly into the exposed disc so that the tip of the probe then resides in the interior of the disc. By this means, radiofrequency or other power sources may be connected to the electrode so as to heat the intervertebral disc directly under open exposure. Monitoring of the disc under such conditions can be done directly at the periphery of the disc. The interruption of the neural structures as described above would also pertain for this "open procedure."

It should be noted that whereas various mechanisms have been put forth here to explain the discovery that heating of a disc will relieve pain, the precise anatomical mechanism of this pain relieving process has not been totally clarified. For example, anatomical material changes within the disc material itself and resulting volumetric changes of the disc may play some role. Spread of the heat to large neural structures in the proximity of the disc may be additional contributory factors of significance. Although the precise neurological origins of the pain relief have not been totally elucidated, nonetheless, this does not diminish the spectacular discovery which is pertinent to this invention, namely that heating of the disc dramatically relieves pain in patients with pain syndromes that are, in some cases, refractory to other clinical modalities that have been heretofore possible.

Figure 7:
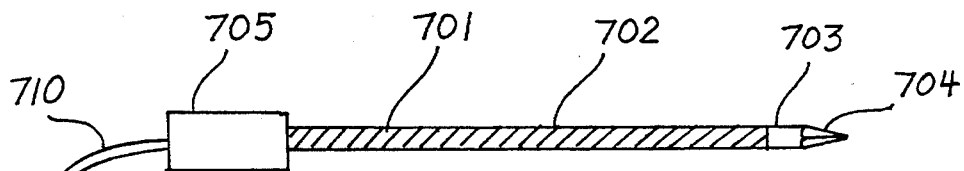
FIG. 7 shows a self-contained needle with pointed tip for tissue penetration, radiolucent hub, and external connection cables.

The present invention includes many other variations that are possible for those skilled in the art. For example, FIG. 7 shows yet another electrode embodiment which requires only one structure to do multiple functions. It consists of a shaft 701 which is insulated over its surface 702 and has an exposed tip 703. The tip, in this case, is illustrated with a point 704 that has a trocar shape, as opposed to a planar, angular bevel. This merely illustrates that there are a variety of ways of implementing a tissue-piercing point. Inside the tip 703 may be a temperature sensor for reading the tissue temperature during heating. The hub 705 is substantially radiolucent so as to enable the possibility of the needle view or tunnel vision radiographic monitoring. A cable 710 connects to the shaft 01, and thus to the exposed tip 703 as a supply of radiofrequency power. This structure can be inserted into the tissue and serve the multiple functions of impedance monitoring, rf power delivery, temperature monitoring, etc. Thus, it obviates the need for multiple cannulae and stylets. It has the obvious deficit that, if one wishes to inject contrast media or local anesthetic, it would not be possible without an open lumen needle cannula, as illustrated in the above figures, or injection and exit holes on the hub and tip of the electrode. However, since injection of such fluids in some situations is not a requirement, the electrode system illustrated in FIG. 7 would be an adequate embodiment of the present invention.

Figure 8:
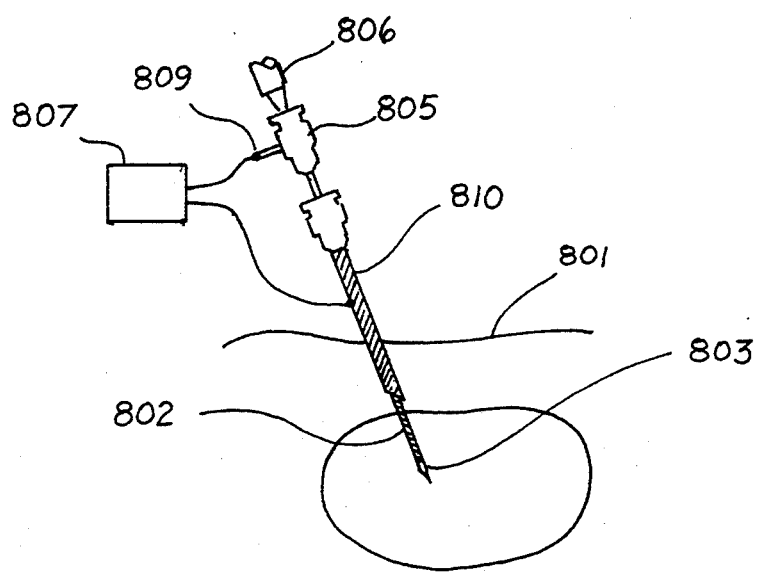
FIG. 8 shows an adjacent needle set for monitoring impedance in a disc during the process of doing anesthetic diagnostic nerve blocks.

FIG. 8 shows another element in the invention which could help to evaluate which disc is causing the pain and should be heated. There may be a relationship between electrical impedance within the disc and the quality or "health" of the disc itself. This can be significant to measure the impedance at the stage where the proper disc to heat is being ascertained by injecting local anesthetic solution into the disc and observing the effect on pain. In FIG. 8, a thin insulated needle 802 is placed into the disc. It has insulated shaft and uninsulated tip 803. Injection of anesthetic can be done through hub 805 and syringe 806. Impedance may be monitored from electrical connection 809 to external apparatus 807, an impedance monitor. Guide cannula 810 may guide needle 801, and could serve as a reference electrode for monitor 807. This impedance monitoring and anesthetic injection could be used as a diagnostic step prior to inserting a probe for heating the disc, and there could be an added stage in the method of the present invention.

There are many variations on the present invention which might be possible. Combinations of impedance monitoring, stimulating, and temperature monitoring in conjunction with the heating method have been described and can be used. It is also not necessary that the source of heating of the disc be radiofrequency current. It could alternatively be microwave current or direct current heating. In the case of direct current heating, one could use for example a nichrome wire inside the probe to create ohmic heat of the tip at a location within the disc. The heat would spread by thermal conduction throughout the disc and give rise to a similar effect on the neural structures as described above. RF heating has advantages in that it deposits the heat energy at longer range relative to the tip, and thus has the feature of distributing the heat throughout the disc in an effective way. The heating may be by penetrating radiation such as ultrasound or microwaves that are absorbed by the disc with or without a probe being placed in the disc. A ferromagnetic seed might be placed in the disc, and it in turn heated by induction from external waves or beams. Thus the "probe" may mean any object placed in the disc that is an agent to cause heating of the disc.

The disc heating may be done in conjunction with other intervertebral surgery or instrumentation. For example, during percutaneous discectomy (partial disc removal as described by Onik, et al.) the tools that are used such as a cutting tool may serve also as a heating probe. The disc heating can be done simultaneously or as an adjunct to other disc treatment. This may as well apply to open surgical laminectomy (disc surgery) at which time tools or probes may serve as agents to heat the disc according to the present invention.

Stereotactic apparatus and other guidance techniques could be used to place the tip of the electrode at a desired target within the disc or at several targets within the disc in sequence. Clusters of heating probes could be used to more effectively deposit heat throughout a volume of a disc. Such variations are obvious to those skilled in the art and are meant to be included in the scope of the present invention.

REFERENCES

1. Cosman B. J., Cosman E. R.: Methods of making nervous system lesions. In Wilkins, R. and Rengachary, S (eds.) *Neurosurgery,* New York, Mc-Graw-Hill, Vol. 3, pp 2490–2499, 1985.
2. Cosman E. R., Nashold B. S., Ovelman-Levitt J.: Theoretical aspects of radiofrequency lesions in the dorsal root entry zone. Neurosurg 15:945–950, 1984.
3. Sluijter M. E.: Percutaneous thermal lesions in the treatment of back and neck pain. *Radionics Procedure Technique Series Monographs.* Burlington, Mass., Radionics, Inc., 1981.
4. Sluijter M. E.: Radiofrequency lesions in the treatment of cervical pain syndromes. *Radionics Procedure Technique Series Monographs.* Burlington, Mass, Radionics, Inc., 1990.
5. Sluijter M. E.: The use of radiofrequency lesions for pain relief in failed back patients. Int. Disabil. Studies, 10:37–43, 1988.
6. Sluijter M. E., Mehta M.: Treatment of chronic back and neck pain by percutaneous thermal lesions. In Lipton, S. and Miles, J. (eds.) *Persistent pain, modern methods of treatment,* Vol. 3, pp 141–179. Academic Press, London., Toronto, and Sydney, 1981.

Having described various embodiments of the present invention, we claim by U.S. Letters Patent the following claims:

1. A method of treating back or neck pain of a patient by heating an intervertebral disc, including:
    (a) Inserting a probe into said disc, said probe being adapted to be connected to external apparatus which can deliver power through said probe to said disc so as to heat said disc;
    (b) Applying said power from said external apparatus to said disc via said probe causing heating of said disc which thereby causes relief of said back pain.

2. The method of claim 1 wherein said probe is a radiofrequency electrode and said external apparatus is a radiofrequency generator, and further including the step of increasing the voltage output of said radiofrequency generator so as to send current through said radiofrequency electrode into said disc and thus heat said disc by ohmic heating.

3. A method of treating back or neck pain of a patient by heating the interior of an intervertebral disc, including the steps of:
    (a) Inserting a probe into said patient so that the tip of said probe is positioned inside said intervertebral disc; said probe being adapted to be connected to external apparatus which is so adapted to generate power that can be transmitted via said probe to said probe tip so as to heat tissue around said probe tip when said probe tip is in said intervertebral disc;
    (b) Applying power from external apparatus to said probe so that said probe tip causes heating of said interior of said intervertebral disc to a temperature substantially above body temperature by absorption of at least a portion of said applied power via said probe tip to the tissue of said intervertebral disc;
    (c) Whereby consequent spread of heat around said probe tip and within said intervertebral disc will cause heating and resultant changes in the disc material and nearby neurological structures, thereby relieving said patient's pain.

4. The method of claim 3 wherein said probe has a temperature sensor in said probe tip, and including the added step of monitoring the temperature of said intervertebral disc by reading out the output of said temperature sensor by external monitoring means, and thereby quantitatively monitoring said heating process of said intervertebral disc.

5. The method of claim 3 in which said external apparatus is a radiofrequency generator, and said probe is a radiofrequency electrode including an elongated metal shaft which is insulated over substantially all of its surface except for an uninsulated rf tip at its far end and including electrical connection means on the other near end of said probe to connect to said radiofrequency generator, and further including the step of electrically connecting the voltage output of said radiofrequency generator to said radiofrequency electrode via said electrical connection means, raising the radiofrequency voltage from said radiofrequency generator so as to create said heating of said intervertebral disc by emission of radiofrequency current created by said radiofrequency generator from said tip of said rf tip.

6. An apparatus for heating the intervertebral disc of a patient for the relief of pain, including:
    (a) an insulated cannula with substantially radiolucent hub and electrically uninsulated conductive tip;
    (b) an obdurating stylet for insertion into said insulated cannula having a substantially radiolucent hub and electrical connection means running within said insulated cannula to connect said uninsulated conductive tip to an external current source;
    (c) whereby, when said insulated cannula is inserted into said patient's body so that said uninsulated tip of said cannula is placed within said intervertebral disc, with said obdurating stylet inserted into said insulated cannula so that said substantially radiolucent cannula hub and said substantially radiolucent stylet hub will present no substantial image or viewing obstruction on an X-ray view which will be taken of said insulated cannula and said stylet when said insulated cannula is being guided into said intervertebral disc, and when said obdurating stylet is connected to said external current source by said electrical connection means, then electrical current from said electrical current source can be caused to flow from said uninsulated tip into said intervertebral disc so as to heat said intervertebral disc and relieve said patient's pain.

7. The apparatus of claim 6 and further including:
    an external impedance monitoring apparatus adapted to be connected to said obdurating stylet by said electrical connection means, whereby during the insertion of said insulated cannula into said intervertebral disc of said patient with said obdurating stylet inserted into said insulated cannula, the tissue impedance of said patient's body can be monitored so as to confirm the proper placement of said uninsulated tip inside of said intervertebral disc.

8. The apparatus of claim 6 and further including:
    an external temperature monitoring apparatus adapted to be connected to said obdurating stylet, said obdurating stylet including temperature sensing means in its tip, which can communicate with said temperature monitoring apparatus by sensor connection means within said obdurating stylet so as to measure the temperature of said temperature sensor;

whereby, when said insulated cannula with said obdurating stylet together are inserted into said intervertebral disc so that said uninsulated tip of said cannula is within said disc and said tip of said obdurating stylet with indwelling said temperature sensor is near said tip of said insulated cannula, the tissue temperature of the intervertebral disc near said uninsulated tip may be monitored during the application of said external current source which heats said intervertebral disc.

9. The apparatus of claim 6 in which the shaft of said insulated cannula is made of a conductive, elongated metal structure with a surface insulation, said metal structure providing connection between said electrically conductive, uninsulated tip to said electrical conduction means.

10. A radiofrequency electrode system for heating the intervertebral disc of a patient, including:
   (a) a cannula with metal tube shaft which is insulated over its surface, except for an uninsulated tip which can deliver radiofrequency current to nearby tissue of said patient when said cannula is inserted into said patient's body, said metal tube shaft of said cannula having an open end at the far end of said cannula, and said cannula having a substantially radiolucent cannula hub at the near end of said cannula;
   (b) a stylet including a metal shaft to fit into said cannula so as to make electrical connection to said metal tube, and to occlude said open end at said far end; and when said stylet is inserted into said cannula, said stylet having a substantially radiolucent stylet hub, and said stylet having electrical connection means adapted to be electrically connected to external impedance monitoring apparatus and to said metal shaft;
   (c) whereby, when said stylet is inserted into said cannula and said cannula is inserted into said intervertebral disc of said patient, said radiolucent hubs enable substantially unobstructed guidance of said electrode by X-ray images of said cannula's uninsulated tip to be placed within said intervertebral disc, and whereby the electrical impedance of said patient's bodily tissue near said uninsulated tip can be monitored so as to determine when said uninsulated tip is within said intervertebral disc.

11. The apparatus of claim 10 and further including:
a radiofrequency probe adapted to be inserted into said cannula, said radiofrequency probe having a metal shaft to make electrical connection to said tube shaft when said radiofrequency probe is inserted into said cannula and therefore making electrical connection to said uninsulated tip, said radiofrequency probe having an rf connection means to an external rf generator, whereby when said uninsulated tip is within said intervertebral disc, said radiofrequency generator can supply radiofrequency current to said cannula and through said uninsulated tip to the tissue of said intervertebral disc so as to heat said intervertebral disc and relieve the pain of said patient related to said intervertebral disc.

12. The apparatus of claim 11 wherein said radiofrequency probe has a temperature sensor within its far end tip to approximate said uninsulated tip of said cannula when said rf probe is inserted fully within said cannula, said electrical connection and said radiofrequency generator being so adapted to provide connections and monitoring means to monitor the temperature read from said temperature sensor when said uninsulated tip is within said intervertebral disc, and whereby the radiofrequency generator has readout means to monitor the heating process of said intervertebral disc.

13. A method of treating back and neck pain of a patient by radiofrequency heating of an intervertebral disc of said patient, including the steps of:
   (a) inserting a radiofrequency electrode into said patient, said radiofrequency electrode having a substantially insulated shaft with an uninsulated conductive radiofrequency tip at its far end, and radiofrequency connections at the other near end, and electrical connections between said radiofrequency connections and said radiofrequency tip, said radiofrequency electrode being adapted to penetrate said patient's body and said intervertebral disc so that said radiofrequency tip may be placed within said intervertebral disc;
   (b) connecting an external radiofrequency generator to said radiofrequency connection so as to apply a radiofrequency voltage generated by said radiofrequency generator to said radiofrequency tip via said electrical connection;
   (c) increasing said radiofrequency voltage to cause current to flow from said radiofrequency tip into said intervertebral disc when said radiofrequency tip is placed within said intervertebral disc, to cause said intervertebral disc to heat up and thus cause changes in said intervertebral disc material and nearby neurological structures, thereby relieving said patient of said pain.

14. The method of claim 13 and further including the steps of: inserting an anesthetic delivery needle into said disc prior to inserting said radiofrequency electrode into said disc, said delivery needle being adapted to monitor impedance in said disc and to inject anesthetic into the region near and in said disc, whereby a diagnostic evaluation of said disc can be made by observing any anesthetic blocking effects or abnormal impedance characteristics of said disc to assess if said disc should be heated.

* * * * *